(12) United States Patent
Qian

(10) Patent No.: US 10,421,708 B2
(45) Date of Patent: Sep. 24, 2019

(54) SENSITIZER FOR UV-LED PHOTOCURING AND PREPARATION METHOD AND USE THEREOF

(71) Applicant: Changzhou Tronly New Electronic Materials Co., Ltd., Changzhou, Jiangsu (CN)

(72) Inventor: Xiaochun Qian, Changzhou (CN)

(73) Assignee: Changzhou Tronly New Electronic Materials Co., Ltd., Jiangsu (CN)

( * ) Notice: Subject to any disclaimer, the term of this patent is extended or adjusted under 35 U.S.C. 154(b) by 0 days.

(21) Appl. No.: 15/738,524

(22) PCT Filed: Jun. 23, 2016

(86) PCT No.: PCT/CN2016/086881
§ 371 (c)(1),
(2) Date: Dec. 20, 2017

(87) PCT Pub. No.: WO2016/206602
PCT Pub. Date: Dec. 29, 2016

(65) Prior Publication Data
US 2018/0186723 A1 Jul. 5, 2018

(30) Foreign Application Priority Data
Jun. 24, 2015 (CN) .......................... 2015 1 0355839

(51) Int. Cl.
| | | |
|---|---|---|
| C07C 51/377 | (2006.01) | |
| C07C 69/86 | (2006.01) | |
| C07C 67/08 | (2006.01) | |
| C07C 69/94 | (2006.01) | |
| G03F 7/004 | (2006.01) | |
| G03F 7/027 | (2006.01) | |
| C07C 67/14 | (2006.01) | |
| G03F 7/031 | (2006.01) | |

(52) U.S. Cl.
CPC ............ *C07C 69/86* (2013.01); *C07C 51/377* (2013.01); *C07C 67/08* (2013.01); *C07C 67/14* (2013.01); *C07C 69/94* (2013.01); *G03F 7/004* (2013.01); *G03F 7/027* (2013.01); *G03F 7/031* (2013.01); *C07C 2601/08* (2017.05); *C07C 2601/14* (2017.05); *C07C 2603/24* (2017.05)

(58) Field of Classification Search
None
See application file for complete search history.

(56) References Cited

U.S. PATENT DOCUMENTS 8,105,759 B2 * 1/2012 Miyasaka ............. G03F 7/0007
430/275.1
2013/0286317 A1 10/2013 Zhong

FOREIGN PATENT DOCUMENTS

| CN | 101218538 | 7/2008 |
| CN | 102660300 | 9/2012 |
| CN | 102876336 | 1/2013 |
| CN | 104991418 | 10/2015 |
| JP | 2014-129498 | 7/2014 |
| JP | 2014-148662 | 8/2014 |
| WO | WO 2005/051332 | 6/2005 |
| WO | WO 2013/159400 | 10/2013 |

OTHER PUBLICATIONS

International Search Report issued in application No. PCT/CN2016/086881 dated Sep. 1, 2016.
Written Opinion received in application No. PCT/CN2016/086881 dated Sep. 1, 2016.

* cited by examiner

*Primary Examiner* — Ana Z Muresan
(74) *Attorney, Agent, or Firm* — Knobbe, Martens, Olson & Bear, LLP

(57) ABSTRACT

The present disclosure provides a sensitizer for UV-LED photocuring, having a chemical structure as represented by formula (I). This sensitizer has a very good adaptability to existing photoinitiators, can significantly improve the curing efficiency under the irradiation of a UV-LED light source when used in a photocurable composition, and has excellent application properties.

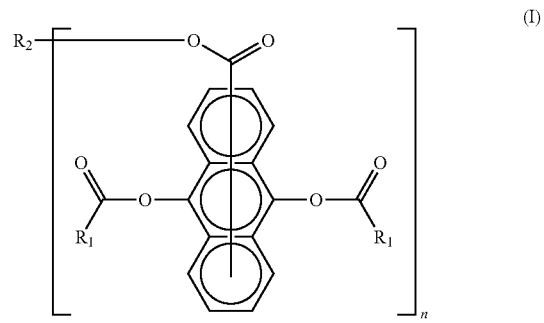

11 Claims, 1 Drawing Sheet

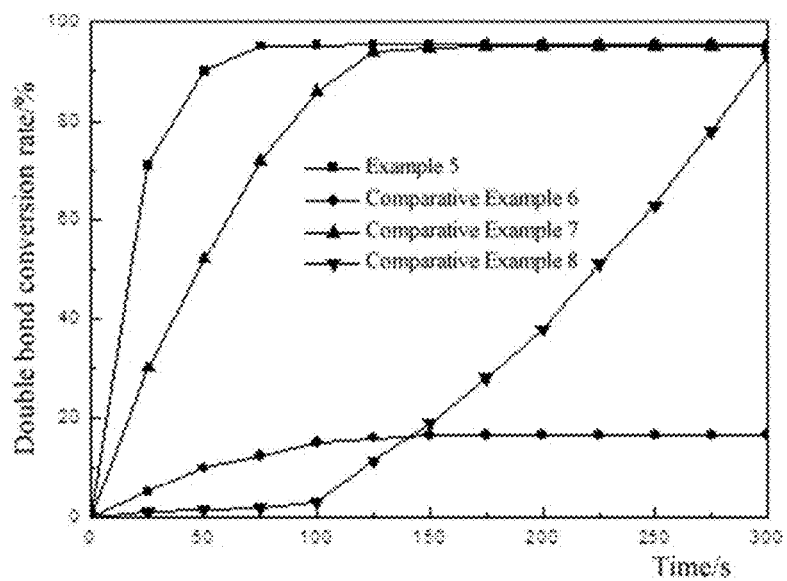

SENSITIZER FOR UV-LED PHOTOCURING AND PREPARATION METHOD AND USE THEREOF

This application is the U.S. National Phase under 35 U.S.C. § 371 of International Application No. PCT/CN2016/086881, filed Jun. 23, 2016, designating the U.S., and published in French as WO 2016/206602 A1 on Dec. 29, 2016, which claims priority to Chinese Patent Application No. 201510355839.1, filed Jun. 24, 2015, the entire contents of which are incorporated herein by reference.

TECHNICAL FIELD

This invention belongs to the field of organic chemistry, and particularly to a sensitizer suitable for an ultraviolet light-emitting diode (UV-LED) photocuring system and a preparation method thereof, as well as its use in the field of photocuring.

BACKGROUND ART

The ultraviolet photocuring technology has extremely broad applications, and the light source used thereby is mainly an ultraviolet light source having a long waveband (such as a mercury lamp). However, this kind of light source has various disadvantages in the process of the development of the photocuring technology, such as, easy generation of ultraviolet light damage, relatively high power consumption, low production efficiency, etc. In view of this, a UV-LED is considered to be an alternate light source having good prospects. It has the characteristic of single-peaked wavelength distribution, and can reduce the damages caused by short-wavelength ultraviolet light and saves power consumption and also contributes to the improvement of production efficiency. However, it is found in applications that a large number of conventional ultraviolet photocuring systems fail to be favorably cured or do not have good curing effects after UV-LED light sources have been used. The reason for this phenomenon is that the transfer of energy fails to be well achieved, and this also becomes a key factor which limits the development and the popularization of the UV-LED photocuring technology.

It is considered through studies that it is an effective approach for solving the problem described above to add a suitable sensitizer to a photocuring system. In the case that a photocurable composition system is not substantially changed, the object of continuously absorbing and transferring energy may be achieved by adding a small amount of sensitizer. With respect to the photocuring technology, this is a low-cost improvement mode and can ensure the advantages of the UV-LED photocuring technology described above. Therefore, the development of a sensitizer which can be fit for existing photoinitiators and is suitable for UV-LED light sources becomes a research hotspot in the field of photocuring currently.

SUMMARY OF INVENTION

This invention first provides a sensitizer for UV-LED photocuring. This sensitizer has a very good adaptability to existing photoinitiators (such as 1173, 184, BDK, 907, etc.), and can significantly improve the curing efficiency under the irradiation of a UV-LED light source when used in a photocurable composition, thereby contributing to the popularization and the development of the UV-LED photocuring technology.

The sensitizer for UV-LED photocuring of this invention has a structure as represented by formula (I):

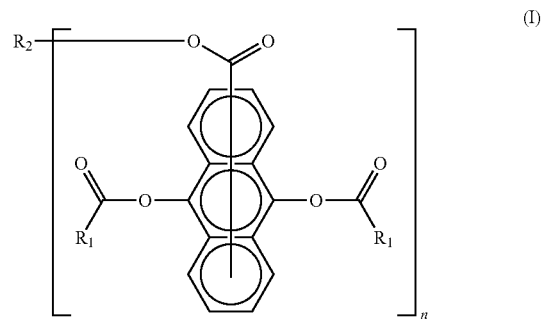

wherein, $R_1$ represents a $C_1$-$C_{20}$ linear or branched alkyl group, a $C_3$-$C_{20}$ cycloalkyl group, or a $C_4$-$C_{20}$ alkylcycloalkyl or cycloalkylalkyl group;

$R_2$ represents a $C_1$-$C_{40}$ n-valent hydrocarbyl group, in which —$CH_2$— may be optionally substituted with an —O— group or a 1,4-phenylene group, provided that two —O— groups are not directly connected with each other;

n represents an integer greater than 0.

Preferably, in the sensitizer represented by formula (I) described above, $R_1$ represents a $C_1$-$C_4$ linear or branched alkyl group, a $C_3$-$C_8$ cycloalkyl group, or a $C_4$-$C_8$ alkylcycloalkyl or cycloalkylalkyl group. Particularly preferably, $R_1$ is selected from the group consisting of a methyl group, an ethyl group, a propyl group, an isopropyl group, a butyl group, a cyclopentyl group, a cyclohexyl group, a cyclopentyl methyl group, and a cyclopentyl ethyl group.

Preferably, in the sensitizer represented by formula (I) described above, $R_2$ represents a $C_1$-$C_{10}$ linear or branched n-valent alkyl group, in which —$CH_2$— may be optionally substituted with an —O— group or a 1,4-phenylene group, provided that two —O— groups are not directly connected with each other.

Particularly preferably, $R_2$ is selected from the group consisting of $CH_3$—, $CH_3CH_2$—, $CH_3CH_2CH_2$—, $CH_3CH_2CH_2CH_2$—, $CH_3$—$(CH_2)_4$—, $CH_3$—$(CH_2)_5$—, $CH_3$—$(CH_2)_6$—, $CH_3$—$(CH_2)_7$—, $C(CH_2$—$)_4$, $CH(CH_2CH_2$—$)_3$, $CH(CH_2CH_2CH_2$—$)_3$, $CH(CH_2$—O—$CH_2$—$)_3$, —$(CH_2)_9$—, —$(CH_2)_2$—O—$(CH_2)_3$—O—$(CH_2)_2$—, and —$C_6H_4$—$C(CH_3)_2$—$C_6H_4$—.

Preferably, in formula (I), n is 1, 2, 3, or 4.

The invention further provides a preparation method of the sensitizer represented by formula (I) described above, comprising the steps of:

(1) performing a reduction reaction on a raw material 1 to generate an intermediate a;

(2) performing a Friedel-Crafts reaction between the intermediate a and an acid chloride $R_1$—CO—Cl in the presence of a catalyst to obtain an intermediate b; and (3) performing an esterification reaction between the intermediate b and an alcohol $R_2$—$(OH)_n$ to obtain a product of interest;

the process formula of the reactions being shown below:

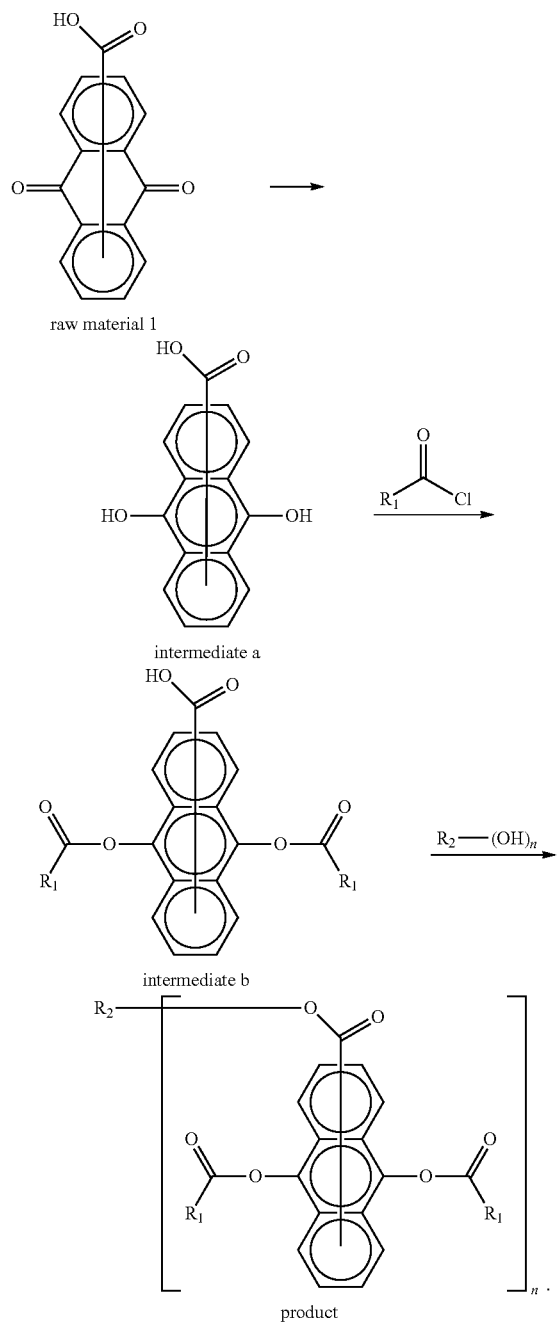

The reduction reaction of step (1) is preferably performed in a solvent containing a reducing agent. The solvent is preferably acetic acid or hydrochloric acid and the reducing agent is preferably zinc powder or iron powder. The temperature of the reaction is typically between 20° C. and 80° C.

The Friedel-Crafts reaction of step (2) is performed in a solution system containing a catalyst. The solvent used in the reaction is not specially limited, as long as reaction agents can be dissolved and there is no adverse influence on the reaction, for example hydrocarbon solvents, such as dichloromethane, dichloroethane, toluene, benzene, xylene, etc. The catalyst is preferably aluminum trichloride. The temperature of the reaction varies according to the type of the reaction agent and is typically between −10° C. and 40° C., which is easily determined by the person skilled in the art.

The esterification reaction of step (3) is performed in the presence of a catalyst. The catalyst is preferably concentrated sulfuric acid. According to the practical situation (such as the type of the reaction agent) in the reaction system, a solvent and/or a polymerization inhibitor may be added selectively or may not be added to the system. Here, the type of the solvent is not particularly limited, as long as it can dissolve reaction agents and there is no adverse influence on the reaction. For example, it may be a conventional hydrocarbon solvent, such as dichloromethane, dichloroethane, toluene, benzene, xylene, etc. The polymerization inhibitor is preferably p-hydroxyanisole. The temperature of the esterification reaction varies according to the type of the reaction agent and is typically between 50° C. and 180° C., which is easily determined by the person skilled in the art.

In the process of preparing the sensitizer represented by formula (I) described above, the reaction agents used are all compounds known in the prior art, may be commercially available or may be conveniently prepared by existing synthetic methods.

The sensitizer represented by formula (I) of this invention can be used in a UV-LED photocuring system. Under the action of the UV-LED light source, this sensitizer has a very good synergistic effect with existing photoinitiators, in particular 1173, 184, BDK, 907, etc., can significantly improve the curing efficiency under the irradiation of a UV-LED light source, and has excellent application properties.

BRIEF DESCRIPTION OF DRAWINGS

The accompanying drawing constituting a part of this application is used to provide further understanding of this invention, schematic examples of this invention and the illustration thereof are used for explaining this invention and do not constitute inappropriate limitations of this invention. In the drawing:

FIG. 1 is a graph of the double bond conversion rate of hydroxyethyl methacrylate in different cases.

DETAILED DESCRIPTION OF EMBODIMENTS

It is to be indicated that examples in this application and features in the examples may be combined with each other without being conflicted. Hereafter, this invention will be further illustrated in detail below in conjunction with specific Examples, but it is not to be understood that the scope of this invention is limited thereto.

As described in the background art, since a large number of existing ultraviolet photocuring systems fail to be favorably cured or do not have good curing effects after UV-LED light sources are used, the development and the popularization of the UV-LED photocuring technology are limited. In order to solve the problem described above, this invention provides a sensitizer for UV-LED photocuring, a preparation method thereof, and use thereof.

In a typical embodiment of this application, there is provided a sensitizer for UV-LED photocuring, having a structure as represented by formula (I):

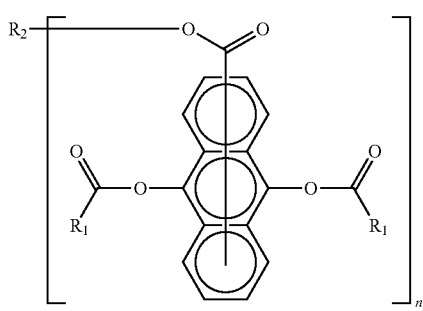

(I)

wherein, $R_1$ represents a $C_1$-$C_{20}$ linear or branched alkyl group, a $C_3$-$C_{20}$ cycloalkyl group, or a $C_4$-$C_{20}$ alkylcycloalkyl or cycloalkylalkyl group; $R_2$ represents a $C_1$-$C_{40}$ n-valent hydrocarbyl group, in which —$CH_2$— may be optionally substituted with an —O— group or a 1,4-phenylene group, provided that two —O— groups are not directly connected with each other; and n represents an integer greater than 0.

This sensitizer has a relatively high ultraviolet absorption wavelength, wherein the parent ring anthracene is the main structure and has an absorption wavelength at about 355 nm. At the meanwhile, an ester group is introduced to the main structure, so that the sensitizer has a sensitizing effect while the ultraviolet absorption wavelength thereof may be further increased. Therefore, the sensitizer can be well fit for UV-LED light sources to improve the curing efficiency of the curing system under the UV-LED light source. At the meanwhile, the applicant has surprisingly found that this sensitizer has a very good adaptability to existing photoinitiators (1173, 184, BDK, 907, etc.), and the curing efficiency under the irradiation of a UV-LED light source can be significantly improved when the combination thereof is used in a photocurable composition. However, the specific principle of achieving the surprising effect described above has not been determined yet, and the applicant infers that this is possibly because the sensitizer of this application has a higher triplet energy level compared to a general sensitizer and can be better fit for photoinitiators.

PREPARATION EXAMPLES

Example 1

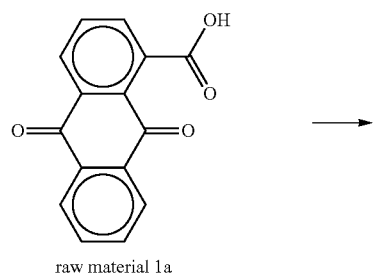

raw material 1a

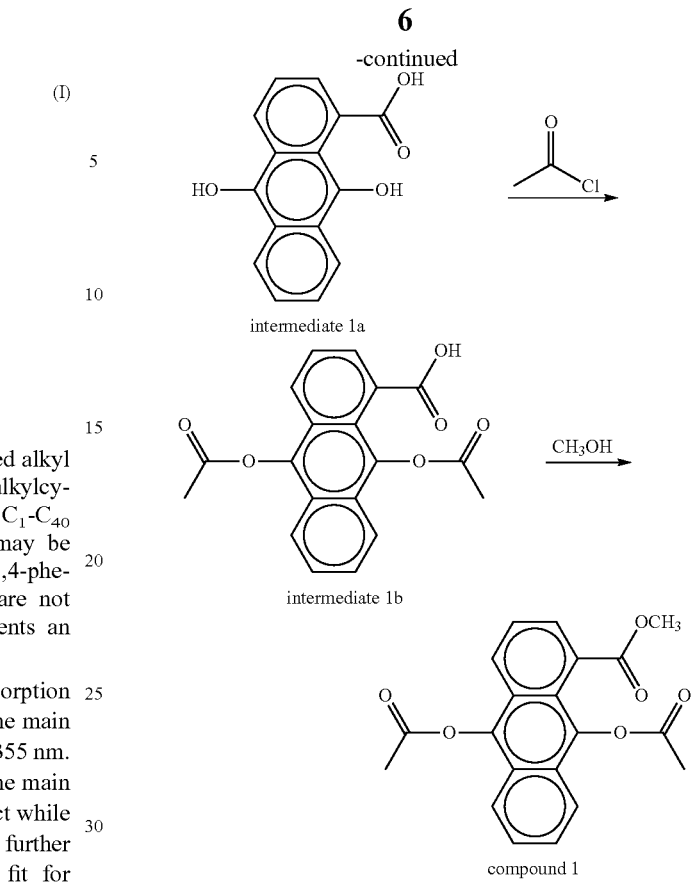

intermediate 1a intermediate 1b compound 1

(1) Preparation of Intermediate 1a

The raw material 1a 126 g, zinc powder 50 g, and acetic acid 100 mL were added to a 500 mL four-necked flask, stirred at room temperature (about 25° C.) for 3 h, and closed for reaction. The reaction solution was filtered with celite and then the filtrate was poured into 500 mL of ice water, and a white solid precipitated with stirring, which was washed with water and dried to obtain the intermediate 1a 122 g.

The structure of the intermediate 1a was confirmed by $^1$H-NMR, and characterization results were as follows.

$^1$H-NMR (CDCl$_3$, 500 MHz): 5.0481-5.3002 (2H, s), 7.3351-8.6179 (7H, m), 10.7352-11.0352 (1H, s).

(2) Preparation of Intermediate 1b 76 g of the intermediate 1a, 100 mL of dichloromethane, and 60 g of aluminum trichloride were added to a 500 mL four-necked flask and stirred with the temperature being controlled at 0° C., 50 mL of a dichloromethane solution containing 48 g of acetyl chloride was then dropped within about 2 h, stirring was continued for 2 h after completion of dropping, and the reaction was tracked by liquid phase chromatography until it was complete. The reaction liquid was poured into 500 mL of a cooled aqueous sodium bicarbonate solution (5 mass %), which was stirred, from which an organic layer was separated and washed with water to become neutral, and a dichloromethane solution of the product was evaporated by rotation to obtain a light yellow solid 93 g, i.e. the intermediate 1b.

The structure of the intermediate 1b was confirmed by $^1$H-NMR, and characterization results were as follows.

$^1$H-NMR (CDCl$_3$, 500 MHz): 2.0012 (6H, s), 7.3481-8.4064 (7H, m), 10.8621-11.1237 (1H, s).

(3) Preparation of Compound 1

The intermediate 1b 68 g, methanol 50 mL, and 70% concentrated sulfuric acid 5 g were added to a 250 mL four-necked flask, and a distillation apparatus and a water trap were connected. 5 mL of toluene was added to the water trap. The reaction was heated to reflux at 70° C., water generated in the reaction was evaporated while the reaction proceeded, and the reaction was tracked by liquid phase chromatography until it did not change anymore to obtain a crude product. The crude product was recrystallized with acetonitrile to obtain a white solid, which was dried to obtain a product 67 g with a purity of 99%, i.e. the compound 1.

The structure of the product was confirmed by $^1$H-NMR, and characterization results were as follows.

$^1$H-NMR (CDCl$_3$, 500 MHz): 2.0804 (6H, s), 3.7892 (3H, s), 7.3593-8.2769 (7H, m).

Example 2

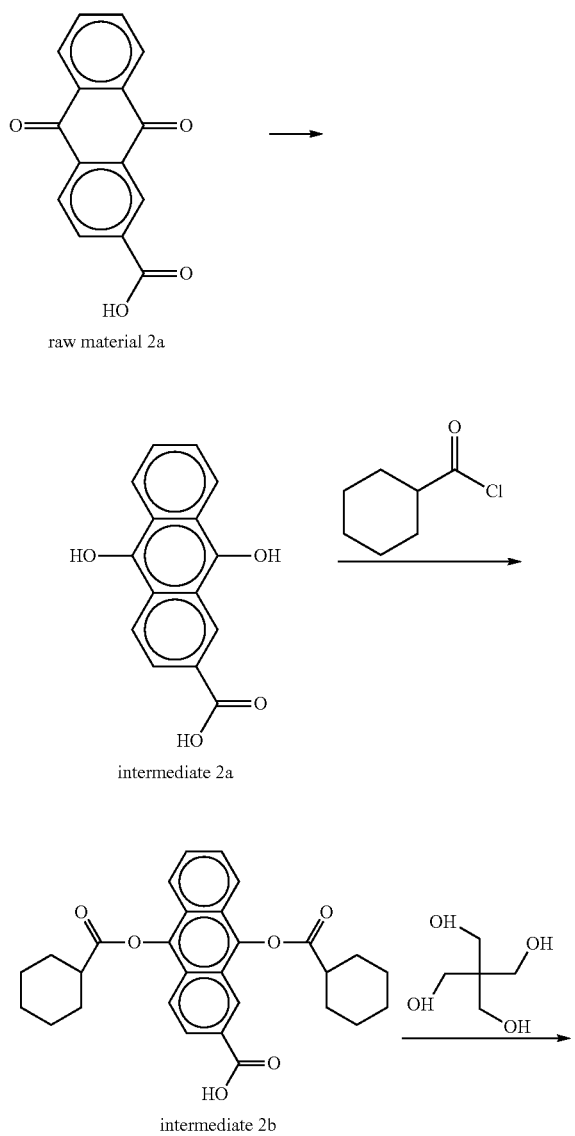

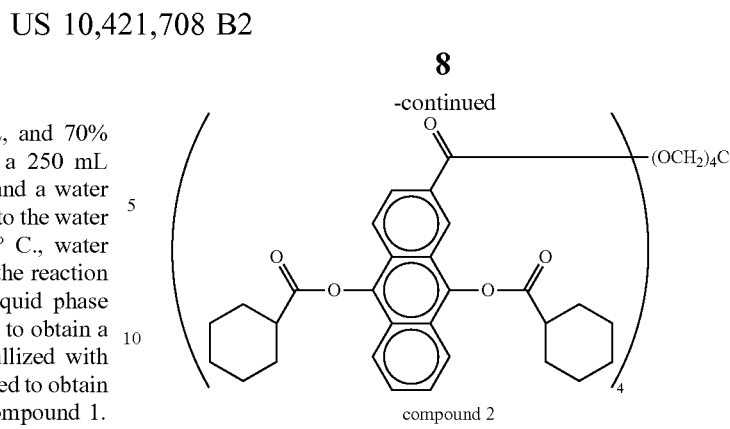

compound 2

(1) Preparation of Intermediate 2a

The raw material 2a 126 g, zinc powder 50 g, and acetic acid 100 mL were added to a 500 mL four-necked flask, stirred at room temperature for 3 h, and closed for reaction. The solution of the product was filtered with celite and then the filtrate was poured into 500 mL of ice water, and a white solid precipitated with stirring, which was washed with water and dried to obtain the intermediate 2a 122 g.

The structure of the intermediate 2a was confirmed by $^1$H-NMR, and characterization results were as follows.

$^1$H-NMR (CDCl$_3$, 500 MHz): 5.0031-5.4321 (2H, s), 7.4453-8.6401 (6H, m), 10.9042-11.2042 (2H, s).

(2) Preparation of Intermediate 2b 76 g of the intermediate 2a, 100 mL of dichloromethane, and 60 g of aluminum trichloride were added to a 500 mL four-necked flask and stirred with the temperature being controlled at 0° C., 50 mL of a dichloromethane solution containing 88 g of cyclohexanecarbonyl chloride was then dropped within about 2 h, stirring was continued for 2 h after completion of dropping, and the reaction was tracked by liquid phase chromatography until it was complete. Next, the reaction liquid was poured into 500 mL of a cooled aqueous sodium bicarbonate solution (5 mass %), which was stirred, from which an organic layer was separated, and washed with water to become neutral, and a dichloromethane solution of the product was evaporated by rotation to obtain a light yellow solid 134 g, i.e. the intermediate 2b.

The structure of the intermediate 2b was confirmed by $^1$H-NMR, and characterization results were as follows.

$^1$H-NMR (CDCl$_3$, 500 MHz): 1.4023-1.4732 (12H, m), 1.6521-1.7034 (8H, m), 2.1032-2.3023 (2H, m), 8.4345-8.9041 (6H, m), 10.9862-11.2032 (2H, s).

(3) Preparation of Compound 2

The intermediate 2b 103 g, pentaerythritol 20 g, 70% concentrated sulfuric acid 8 g, and toluene 100 mL were added to a 500 mL four-necked flask, and a distillation apparatus and a water trap were connected. 5 mL of toluene was added to the water trap. The reaction was heated to reflux at 110° C., water generated in the reaction was evaporated while the reaction proceeded, and the reaction was tracked by liquid phase chromatography until it did not change anymore. Next, redundant toluene was removed by distillation, pentaerythritol was removed by washing with water, and recrystallization was performed with petroleum ether to obtain a white viscous matter 103 g with a yield of 94% and a purity of 99%, i.e. the compound 2.

The structure of the product was confirmed by $^1$H-NMR, and characterization results were as follows.

$^1$H-NMR (CDCl$_3$, 500 MHz): 1.4042-1.5149 (24H, m), 1.6687-1.7218 (16H, m), 2.2546-2.3302 (4H, m), 4.1982 (8H, s), 7.5193-8.6769 (28H, m).

Examples 3-10

With reference to the methods of Examples 1 and 2, compounds 3-10 were synthesized, and the structures thereof and corresponding $^1$H-NMR data were listed in Table 1.

TABLE 1

| | Structural formula | $^1$H-NMR |
|---|---|---|
| Compound 3 | | 0.9982-1.2318(6H, t)<br>2.1975-2.3056(4H, m)<br>3.8876(3H, s)<br>7.3444-8.2875(7H, m) |
| Compound 4 | | 1.0031-1.3155(9H, m)<br>2.2007-2.3132(4H, m)<br>4.2866-4.3421(3H, m)<br>7.3328-8.2991(7H, m) |
| Compound 5 | | 1.2981-1.3021(3H, t)<br>1.4371-1.5143(16H, m)<br>2.1897-2.2076(6H, m)<br>4.3899-4.3008(2H, m)<br>7.3781-8.2667(7H, m) |
| Compound 6 | | 0.9676-1.3305(16H, m)<br>1.7566-1.7621(2H, m)<br>2.2667-2.31793(4H, m)<br>4.2420-4.2508(2H, t)<br>7.3428-8.2661(7H, m) |
| Compound 7 | | 1.0088-1.1342(9H, t)<br>1.6998-1.7128(6H, m)<br>2.2677-2.3741(6H, m)<br>2.6066-2.7022(1H, m)<br>4.2113-4.3088(6H, m)<br>7.3387-8.2616(7H, m) |

TABLE 1-continued

| | Structural formula | $^1$H-NMR |
|---|---|---|
| Compound 8 | (anthracene diester structure with isobutyryl groups and —(OCH$_2$CH$_2$)$_3$CH side chain) | 1.0866-1.1654(12H, d)<br>2.4038-2.5009(1H, m)<br>2.6512-2.7586(2H, m)<br>3.0827-3.3231(6H, m)<br>7.3243-8.2221(6H, m) |
| Compound 9 | (anthracene diester structure with cyclopentyl propanoate groups and —(OCH$_2$CH$_2$OCH$_2$)$_2$CH$_2$ linker) | 1.4771-1.5238(44H, m)<br>1.6362(2H, m)<br>2.2399-2.3217(8H, m)<br>3.3772-3.3838(4H, m)<br>3.8009-3.8442(4H, m)<br>4.4009-4.5112(4H, m)<br>7.3228-8.1108(14H, m) |
| Compound 10 | (bis-anthracene diester structure connected via bisphenol linker) | 1.0002-1.1228(12H, t)<br>1.6129-1.7278(6H, d)<br>2.2011-2.3115(8H, m)<br>7.1087-8.4267(22H, m) |

Property Evaluation

The application properties of the sensitizer represented by formula (I) of this invention were evaluated by formulating an exemplary photocurable composition (i.e., a photosensitive resin composition).

1. Formulation of Photosensitive Resin Composition

A photosensitive resin composition was formulated with reference to the proportions as follows and particular formulations shown in Table 2.

| | |
|---|---|
| A: acrylate copolymer [benzyl methacrylate/methacrylic acid/hydroxyethyl methacrylate (molar ratio: 70/10/20) copolymer (Mw: 10000)] | 200 parts by mass |
| B: dipentaerythritol hexaacrylate | 100 parts by mass |
| C: photoinitiator | 5 parts by mass |
| D: butanone (solvent) | 900 parts by mass |
| E: sensitizer | 0-1 parts by mass |

TABLE 2

| | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|
| A | 200 | 200 | 200 | 200 | 200 | 200 | 200 | 200 | 200 |
| B | 100 | 100 | 100 | 100 | 100 | 100 | 100 | 100 | 100 |
| C1 | 5 | | | | 5 | | | | |
| C2 | | 5 | | | | 5 | | | 5 |
| C3 | | | 5 | 5 | | | 5 | 5 | |
| D | 900 | 900 | 900 | 900 | 900 | 900 | 900 | 900 | 900 |
| E1 | 0.2 | | | | | | | | |
| E2 | | 0.2 | | 0.2 | | | | | |
| E3 | | | 0.2 | | | | | | |

C1 = photoinitiator 1173;
C2 = photoinitiator 184;
C3 = photoinitiator 907;
E1 = Compound 1;
E2 = Compound 8;
E3 = Compound 10

2. Test of Film-Forming Property
(1) Test of Film-Forming Property Under High-Pressure Mercury Lamp The composition described above was stirred under a yellow light lamp. Materials were taken on a PET template and roll coating was performed to form a film, the solvent was removed by drying at 90° C. for 5 min, and a coating film with a film thickness of about 2 μm was formed. A substrate formed with the coating film was cooled to room temperature, and the coating film was exposed with an exposure time of 120 s by irradiating with a high-pressure mercury lamp (exposure machine model: RW-UV70201, light intensity: 50 mW/cm$^2$) to observe whether it can be cured to form a film.

(2) Test of Film-Forming Property Under UV-LED Light Source

The composition described above was stirred under protection from light. Materials were taken on a PET template, film coating was performed with a wire bar, the solvent was removed by drying at 90° C. for 5 min, and a coating film with a film thickness of about 2 μm was formed. A substrate formed with the coating film was cooled to room temperature, and the coating film was exposed at a wavelength of 395 nm with an exposure time of 120 s by irradiating with a UV-LED light source (Shenzhen Lamplic Technology Co., Ltd., model: UVEL-ET, light intensity: 500 mW/cm$^2$) to observe whether it can be cured to form a film.

The test results are as shown in Table 3.

full-waveband point light source and a UV-LED point light source to compare double bond conversion rates under the irradiation of different light sources in cases where the sensitizer was added or was not added.

The higher the double bond conversion rate was, the faster the double bond conversion rate was, indicating a better curing effect. The conditions of formulations of compositions for test and conditions of light sources were as shown in Table 4.

TABLE 4

|  |  | Parts by mass | Example 5 | Comparative Example 6 | Comparative Example 7 | Comparative Example 8 |
|---|---|---|---|---|---|---|
| Photosensitive resin composition | Monomer | 100 | Hydroxyethyl methacrylate | | | |
|  | Photoinitiator | 3 | 184 | | | |
|  | Solvent | 25 | Butanone | | | |
|  | Sensitizer (Compound 1) | 0.2 | Added | Not added | Added | Not added |
|  | Light source |  | UV-LED (UVEL-ET) | | Mercury lamp (RW-UV70201) | |

The compositions having the formulations described above were respectively uniformly mixed and coated on a KBr salt sheet, then placed into Nicolet5700, and irradiated with different point light sources. The ultraviolet light intensity of the surface of the sample was adjusted to 35 mW/cm$^2$, the double bond conversion rates of monomers were collected with near-infrared in real time, the collection time was set to 300 s, and the degree of the change of the polymerization reaction was observed by using the change of the characteristic absorption peak of the carbon-carbon double bond in hydroxyethyl methacrylate. The double bond conversion rate (DC) was obtained by calculation with OMNIC7.1 infrared software and Origin 7.5 data processing software in conjunction with the following formula:

$$DC\ (\%) = [1 - (At/Ao)] * 100\%$$

In the formula, Ao and At were respectively areas of characteristic absorption peaks of the double bond in

TABLE 3

|  | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|
| Type of light source | UV-LED | | | | | | | Mercury lamp | |
| Whether cured to form a film | Yes | Yes | Yes | Yes | No | No | No | Yes | Yes |

As can be seen from Table 3, the photosensitive resin composition containing the photoinitiator can be favorably cured under the irradiation of a mercury lamp (Comparative Examples 4 and 5), and cannot be cured under the irradiation of a UV-LED light source (Comparative Examples 1-3). After a small amount of the sensitizer of this invention was added, the photocuring system under the irradiation of a UV-LED light source can be favorably cured (Examples 1-4). This demonstrated that the sensitizer of this invention had a good applicability under a UV-LED photocuring system.

3. Evaluation on Sensitizing Property

By using real-time infrared detection, the sensitizing property of the sensitizer was evaluated under an ultraviolet hydroxyethyl methacrylate at 1630 cm$^{-1}$ before the sample was cured and at time t after the sample was irradiated.

The test results are as shown in FIG. 1.

As can be seen from FIG. 1, under the irradiation of an ultraviolet full-waveband point light source, even if the sensitizer was not added (Comparative Example 8), the resin composition can be favorably cured. However, the curing speed is relatively slower at the initial stage, the double bond conversion rate at 100 s was merely less than 5%. However, after a small amount of the sensitizer of this invention was added (Comparative Example 7), the curing speed was remarkably accelerated, and the double bond conversion rate at 100 s was up to about 85%.

Under the irradiation of a UV-LED point light source, the curing speed and the double bond conversion rate were very low when the sensitizer of this invention was not added (Comparative Example 6). The double bond conversion rate was merely about 15% even at 300 s. However, after a small amount of the sensitizer of this invention was added (Example 5), both the curing speed and the double bond conversion rate were significantly improved. The double bond conversion rate at 75 s may be up to about 95%.

Additionally, it was worth mentioned that as can be seen from Example 5 and Comparative Example 7, with respect to the sensitizer-containing compositions having the same formulation, the final double bond conversion rates under the irradiation of two light sources were equivalent, but the curing speed under the irradiation of a UV-LED point light source was remarkably higher than that under the irradiation of an ultraviolet full-waveband point light source.

In summary, it can be known that after the sensitizer shown in formula (I) disclosed in this invention was used in a conventional ultraviolet photocuring system, it can be well matched and used with a UV-LED light source, so that the defect of low curing efficiency of a conventional photocuring system under the irradiation of a LED light source can be solved.

Those described above are merely preferred examples of this invention, and are not intended to limit this invention. With respect to the person skilled in the art, there may be various modifications and variations of this invention. All of modifications, equivalent replacements, improvements, and the like, which are within the spirit and the principle of this invention, should be encompassed in the scope protected by this invention.

What is claimed is:

1. A sensitizer for UV-LED photocuring, having a structure of formula (I):

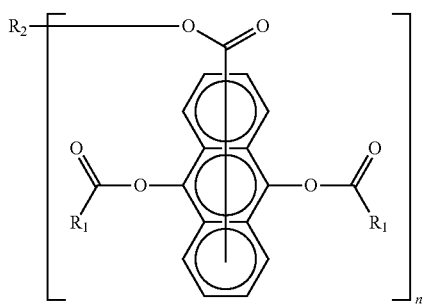

(I)

wherein,
$R_1$ represents a $C_1$-$C_{20}$ linear or branched alkyl group, a $C_3$-$C_{20}$ cycloalkyl group, or a $C_4$-$C_{20}$ alkylcycloalkyl or cycloalkylalkyl group;
$R_2$ represents a $C_1$-$C_{40}$ n-valent hydrocarbyl group, in which —$CH_2$— may be optionally substituted with an —O— group or a 1,4-phenylene group, provided that two —O— groups are not directly connected with each other;
n is 1, 2, 3, or 4.

2. The sensitizer according to claim 1, wherein in the structure of formula (I), $R_1$ represents a $C_1$-$C_4$ linear or branched alkyl group, a $C_3$-$C_8$ cycloalkyl group, or a $C_4$-$C_8$ alkylcycloalkyl or cycloalkylalkyl group.

3. The sensitizer according to claim 1, wherein in the structure of formula (I), $R_1$ is selected from the group consisting of a methyl group, an ethyl group, a propyl group, an isopropyl group, a butyl group, a cyclopentyl group, a cyclohexyl group, a cyclopentyl methyl group, and a cyclopentyl ethyl group.

4. The sensitizer according to claim 1, wherein in the structure of formula (I), $R_2$ represents a $C_1$-$C_{10}$ linear or branched n-valent alkyl group, in which —$CH_2$— may be optionally substituted with an —O— group or a 1,4-phenylene group, provided that two —O— groups are not directly connected with each other.

5. The sensitizer according to claim 1, wherein in the structure of formula (I), $R_2$ is selected from the group consisting of $CH_3$—, $CH_3CH_2$—, $CH_3CH_2CH_2$—, $CH_3CH_2CH_2CH_2$—, $CH_3$—$(CH_2)_4$—, $CH_3$—$(CH_2)_5$—, $CH_3$—$(CH_2)_6$—, $CH_3$—$(CH_2)_7$—, $C(CH_2$-$)_4$, $CH(CH_2CH_2$-$)_3$, $CH(CH_2CH_2CH_2$-$)_3$, $CH(CH_2$—O—$CH_2$-$)_3$, —$(CH_2)_9$—, —$(CH_2)_2$—O—$(CH_2)_3$—O—$(CH_2)_2$—, and —$C_6H_4$—$C(CH_3)_2$—$C_6H_4$—.

6. A preparation method for the sensitizer according to claim 1, comprising:
(1) performing a reduction reaction on a raw material 1 to generate an intermediate a;
(2) performing a Friedel-Crafts reaction between the intermediate a and an acid chloride $R_1$—CO—Cl in the presence of a catalyst to obtain an intermediate b; and
(3) performing an esterification reaction between the intermediate b and an alcohol $R_2$—$(OH)_n$ to obtain a product having a structure of formula (I);
the process formula of the reactions being shown below:

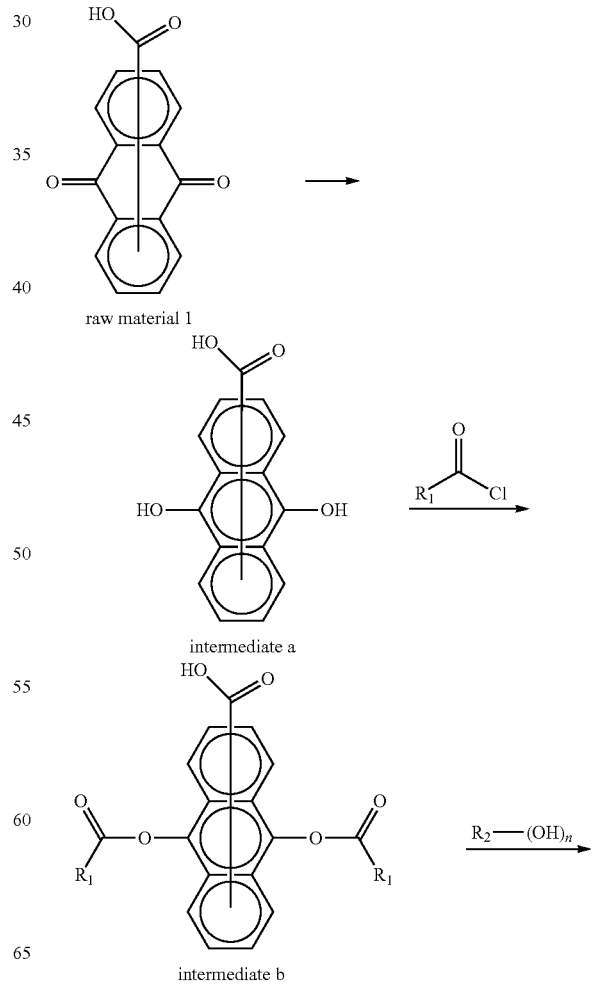

-continued

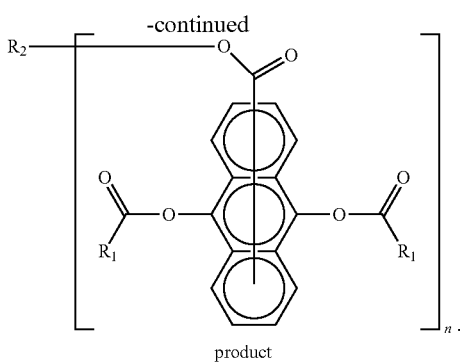

product

7. The preparation method according to claim 6, wherein the reduction reaction of step (1) is performed in a solvent containing a reducing agent, wherein the solvent is acetic acid or hydrochloric acid, and the reducing agent is zinc powder or iron powder.

8. The preparation method according to claim 6, wherein in the reaction of step (2), the catalyst is aluminum trichloride.

9. The sensitizer according to claim 1 in a UV-LED photocuring system.

10. The sensitizer according to claim 2, wherein in the structure of formula (I), $R_1$ is selected from the group consisting of a methyl group, an ethyl group, a propyl group, an isopropyl group, a butyl group, a cyclopentyl group, a cyclohexyl group, a cyclopentyl methyl group, and a cyclopentyl ethyl group.

11. The sensitizer according to claim 4, wherein in the structure of formula (I), $R_2$ is selected from the group consisting of $CH_3$—, $CH_3CH_2$—, $CH_3CH_2CH_2$—, $CH_3CH_2CH_2CH_2$—, $CH_3$—$(CH_2)_4$—, $CH_3$—$(CH_2)_5$—, $CH_3$—$(CH_2)_6$—, $CH_3$—$(CH_2)_7$—, $C(CH_2\text{-})_4$, $CH(CH_2CH_2\text{-})_3$, $CH(CH_2CH_2CH_2\text{-})_3$, $CH(CH_2$—O—$CH_2\text{-})_3$, —$(CH_2)_9$—, —$(CH_2)_2$—O—$(CH_2)_3$—O—$(CH_2)_2$—, and —$C_6H_4$—$C(CH_3)_2$—$C_6H_4$—.

* * * * *